(12) United States Patent
Wang

(10) Patent No.: US 7,520,960 B2
(45) Date of Patent: Apr. 21, 2009

(54) METHOD FOR REDUCING SLIME PRODUCTION AND MIXTURE MAKING THE SAME

(75) Inventor: Jihn-Yuh Wang, Taipei (TW)

(73) Assignee: Yuen Foong Yu Paper Mfg. Co. Ltd. (TW)

( * ) Notice: Subject to any disclaimer, the term of this patent is extended or adjusted under 35 U.S.C. 154(b) by 301 days.

(21) Appl. No.: 11/467,395

(22) Filed: Aug. 25, 2006

(65) Prior Publication Data

US 2006/0283568 A1 Dec. 21, 2006

Related U.S. Application Data

(63) Continuation-in-part of application No. 10/335,314, filed on Dec. 31, 2002, now abandoned.

(30) Foreign Application Priority Data

Oct. 18, 2002 (TW) .............................. 91124140 A

(51) Int. Cl.
*D21H 21/04* (2006.01)
*C12N 1/20* (2006.01)

(52) U.S. Cl. .................... 162/199; 162/161; 162/189; 510/247; 510/421; 210/749; 210/611; 422/28; 422/37; 424/93.1

(58) Field of Classification Search ................ 162/161, 162/180, 189–191, 199; 210/749, 764, 765, 210/606, 611, 620, 631; 510/247, 421, 427; 422/28, 32, 37; 424/93.1, 93.4, 93.43
See application file for complete search history.

(56) References Cited

U.S. PATENT DOCUMENTS

| | | | | |
|---|---|---|---|---|
| 2,046,614 A | | 7/1936 | Drewsen | |
| 2,564,430 A | * | 8/1951 | Gillaspie | 162/161 |
| 2,771,823 A | * | 11/1956 | Lukemire | 162/190 |
| 2,873,249 A | | 2/1959 | Schwartz | |
| 2,881,070 A | * | 4/1959 | Pera | 162/161 |
| 2,881,071 A | | 4/1959 | Buckman et al. | |
| 3,052,605 A | * | 9/1962 | Hagemann et al. | 424/122 |
| 3,140,974 A | | 7/1964 | Pera et al. | |
| 3,151,020 A | | 9/1964 | Cruickshank | |
| 3,250,667 A | | 5/1966 | Legator | |
| 3,582,463 A | * | 6/1971 | Schwerdle | 162/161 |
| 3,780,172 A | * | 12/1973 | Takeda et al. | 424/122 |
| 3,931,038 A | * | 1/1976 | Mochi-Bartolani et al. | 252/181 |
| 3,984,390 A | | 10/1976 | Umezawa et al. | |
| 4,049,417 A | | 9/1977 | Witzel et al. | |
| 4,119,537 A | | 10/1978 | Finkelstein | |
| 4,295,932 A | | 10/1981 | Pocius | |
| 4,370,199 A | | 1/1983 | Orndorff | |
| 4,673,509 A | | 6/1987 | Davis et al. | |
| 4,684,469 A | | 8/1987 | Pedersen et al. | |
| 4,692,316 A | * | 9/1987 | Greaves et al. | 422/16 |
| 4,746,511 A | | 5/1988 | Kobatake et al. | |
| 5,238,572 A | * | 8/1993 | Hernandez-Mena et al. | 210/632 |
| 5,242,593 A | | 9/1993 | Oberkofler et al. | |
| 5,395,530 A | | 3/1995 | Robertson et al. | |
| 5,416,109 A | | 5/1995 | Donofrio et al. | |
| 5,611,939 A | | 3/1997 | Hernandez-Mena et al. | |
| 5,624,575 A | | 4/1997 | Meade et al. | |
| 5,695,652 A | | 12/1997 | Hernandez-Mena et al. | |
| 5,702,605 A | | 12/1997 | Hatanaka | |
| 5,874,453 A | * | 2/1999 | Oppong et al. | 514/367 |
| 5,989,391 A | | 11/1999 | Watanabe et al. | |
| 6,159,999 A | | 12/2000 | Yagi et al. | |
| 6,281,002 B1 | * | 8/2001 | Moller-Bremer | 435/262.5 |
| 6,514,458 B1 | | 2/2003 | Czechowski et al. | |
| 6,660,168 B2 | * | 12/2003 | Sweeny et al. | 210/739 |
| 2003/0155090 A1 | | 8/2003 | Holmberg et al. | |
| 2004/0074621 A1 | | 4/2004 | Wang | |
| 2004/0084383 A1 | | 5/2004 | Zhou et al. | |
| 2004/0132095 A1 | | 7/2004 | Iizumi et al. | |
| 2006/0283568 A1 | * | 12/2006 | Wang | 162/161 |

FOREIGN PATENT DOCUMENTS

| | | | |
|---|---|---|---|
| DE | 10035547 A1 | | 1/2002 |
| EP | 255239 A1 | | 2/1988 |
| EP | 338439 A1 | * | 10/1989 |
| EP | 372520 A2 | | 6/1990 |
| EP | 1413675 A1 | * | 4/2004 |
| JP | 05170602 A | * | 7/1993 |
| JP | 10096194 A | * | 4/1998 |
| JP | 2001348797 A | * | 12/2001 |
| JP | 2002205902 A | * | 7/2002 |
| JP | 2003020598 A | * | 1/2003 |
| JP | 2003306893 A | * | 10/2003 |
| JP | 2004137650 A | * | 5/2004 |
| WO | WO 9902037 A1 | * | 1/1999 |

* cited by examiner

*Primary Examiner*—José A Fortuna
(74) *Attorney, Agent, or Firm*—Alston & Bird LLP

(57) ABSTRACT

A method for reducing a production of a build-up slime in a papermaking process is provided. The method includes steps of adding a dispersing agent into the papermaking material to obtain a first mixture, mixing and culturing the first mixture, adding an antagonist into the first mixture to obtain a second mixture, mixing and culturing the second mixture for reducing the production of the slime, and re-adding the antagonist into the mixed and cultured second mixture after a specific time period for further reducing the production of the slime.

10 Claims, No Drawings icity of the microorganism, e.g., temperature, pH, and nutrition.

METHOD FOR REDUCING SLIME PRODUCTION AND MIXTURE MAKING THE SAME

This is a continuation-in-part application of U.S. patent application Ser. No. 10/335,314 filed on Dec. 31, 2002, now abandoned, the contents of which are incorporated herewith for reference.

FIELD OF THE INVENTION

The present invention relates to a method for reducing production of slime and a mixture making the same, and more particularly to a method and mixture for reducing production of slime by utilizing a dispersing agent and a benefit microorganism having an inhibition/sterilization ability.

BACKGROUND OF THE INVENTION

During a papermaking process, the waste pulp is always recycled. However, because a starch and a coating in the waste paper provide an excellent nutrition source, it believed that they are the main contaminating source for the microorganisms including bacteria and fungus. Otherwise, for reducing consumption of the water, the papermaking factory usually adopts an airtight water cycle system. However, this condition also provides favorable growth conditions for every kind of microorganism, e.g., temperature, pH, and nutrition. Consequently, a multiplicity and growth of the microorganism will be more intensified so as to cause a problem of an excess of microorganism. The formation of slime at the wet end of the papermaking process is a very serious problem in the papermaking factory.

A slime produced at the wet end during the papermaking process will cause the problems of foul smell, paper break and holey, and foxing. All these problems will seriously influence the paper quality and then cause a business trouble which will not only increase the cost owing to the indemnity, but also destroy the reputation.

For preventing the production of the slime, most papermaking factories mainly utilize an organic biocide to reduce the amount of the slime producing microorganisms in the papermaking process and further reduce the slime production so as to solve the problems caused by the slime, e.g., holes in the paper and paper break. However, because the chemical synthesized biocides all are potentially or immediately poisonous to the environment, human beings, and animals, and also because of environmental consciousness, the standards for how to use and dispose the harmful chemicals have become increasingly strict. Consequently, looking for a non-poisonous and unharmful natural prevention method is an important challenge, and research into a mixture which utilizes a local screened antagonist is one topic thereof.

SUMMARY OF THE INVENTION

It is therefore an object of the present invention to reduce the slime production during the papermaking process so as to solve the problems caused by slime.

It is a further object of the present invention to add a benefit microorganism, which does not cause the slime, into a system including white water and substances for preventing or reducing the production of slime.

It is an additional object of the present invention to add a dispersing agent which has an ability of inhibiting the adhesion between the microorganism and the additives during the papermaking process so as to achieve the purpose of inhibiting or reducing a production of slime.

In accordance with one aspect of the present invention, a method for reducing a production of build-up slime of a papermaking material consisting essentially of a white water and a waste paper pulp in a papermaking process is provided. The method includes steps of: adding a dispersing agent into the papermaking material to obtain a first mixture; mixing and culturing the mixture; adding an antagonist into the first mixture to obtain a second mixture; mixing and culturing the second mixture for reducing the slime; and re-adding the antagonist into the mixed and cultured second mixture after a specific time period for further reducing the slime, wherein the antagonist is a microorganism being *Streptomyces bikiniensis*.

Preferably, the antagonist is in an amount of $10^7$/mL after being cultivated for 24 hrs.

Preferably, the dispersing agent is selected from a group consisting of Lignosulfonate, Di-alkyl sulfosuccinate, and Nonionic surfactants).

Preferably, the specific time period is seven days.

In accordance with another aspect of the present invention, a method for reducing a production of build-up slime of a papermaking material consisting essentially of a white water and a leaf bleached kraft pulp in a papermaking process is provided. The method includes steps of: adding a dispersing agent into the papermaking material to obtain a first mixture; mixing and culturing the first mixture; adding an antagonist into the first mixture to obtain a second mixture; and mixing and culturing the second mixture for reducing the slime, wherein the antagonist is a microorganism being *Streptomyces bikiniensis*.

Preferably, the antagonist is in an amount of $10^7$/mL after being cultivated for 24 hrs.

Preferably, the dispersing agent is selected from a group consisting of Lignosulfonate, Di-alkyl sulfosuccinate, and Nonionic surfactants.

In accordance with another aspect of the present invention, a mixture for reducing a production of build-up slime in a papermaking process is provided. The mixture includes a papermaking material consisting essentially of a white water and a leaf bleached kraft pulp, a dispersing agent, and an antagonist being microorganism *Streptomyces bikiniensis*.

Preferably, the antagonist is in an amount of $10^7$/mL after being cultivated for 24 hrs.

Preferably, the dispersing agent is selected from a group consisting of Lignosulfonate, Di-alkyl sulfosuccinate, and Nonionic surfactants.

DETAILED DESCRIPTION OF THE PREFERRED EMBODIMENTS

The present invention will now be described more specifically with reference to the following embodiments. It is to be noted that the following descriptions of preferred embodiments of this invention are presented herein for purpose of illustration and description only; it is not intended to be exhaustive or to be limited to the precise form disclosed.

EXAMPLE 1

The Effect of the Antagonist and the Dispersing Agent on the Formation of the Deposit The experimental steps are described as follows:

Cultures which are isolated from the slime are cultivated in a NB cultivation liquid for 21-24 hours. Then, 1 mL culture liquids of the isolated cultures are centrifuged in 15000 rpm for 1 min and the supernatants thereof are removed. All the isolated cultures are re-suspended by adding 1 mL sterile water, and then each re-suspended culture is inoculated into a flask which already contains sterile white water 100 mL and 3 g LBKP pulp. Later, different dispersing agents are added into different flasks of each kind of culture to obtain different mixtures. The mixtures are cultivated in an incubate shaker at 40° C., 70 rpm. After being mixture cultivated for 3 hours, 3 mL antagonist C5 (*Streptomyces bikiniensis*) which has been amounted to $10^7$/mL after being cultivated for 24 hours is added thereinto to obtain another mixture. The mixture are cultivated in the incubate shaker again at 40° C., 70 rpm. After 7 days, the production of the deposit is recorded.

The whole experiment is separated into six groups.

There are two contrast groups:

1: Only incubate the antagonist C5 without incubating the culture isolated from the slime; and 2: Do not incubate any culture.

There are four experimental group:

3: Only incubate the culture isolated from the slime without incubating the antagonist C5;

4: Incubate both the culture isolated from the slime and the antagonist C5;

5: Incubate the culture isolated from the slime and the dispersing agent; and

6: Incubate the culture isolated from the slime, the dispersing agent, and the antagonist C5.

The groups described above are double checked and all experiments are repeated at least once. Deposit % is calculated by the formula as follows:

$$\text{Deposit}\% = \frac{\text{Deposit dry weight of experimental group}}{\text{Deposit dry weight of the culture isolated from slime}} \times 100\%$$

Results:

The experimental results of "The effect of the antagonist and the dispersing agent on the formation of the deposit" are shown in Table 1.

TABLE 1

The result of the effect of adding antagonist and disperaing agent on the slime formation.

| Process method | Deposit (%) of the slime |
|---|---|
| Culture isolated from slime | 100.0 |
| Isolated culture + dispersing agent B100 | 113.0 |
| Isolated culture + dispersing agent S100 | 53.0 |
| Isolated culture + dispersing agent H40 | 126.0 |
| Isolated culture + dispersing agent P100 | 112.0 |
| Isolated culture + dispersing agent Bu200 | 211.0 |
| Isolated culture + Antagonist C5 | 53.0 |
| Isolated culture + dispersing agent B100 + Antagonist C5 | 74.6 |
| Isolated culture + dispersing agent S100 + Antagonist C5 | 49.0 |
| Isolated culture + dispersing agent H40 + Antagonist C5 | 46.0 |
| Isolated culture + dispersing agent P100 + Antagonist C5 | 105.0 |
| Isolated culture + dispersing agent Bu200 + Antagonist C5 | 66.4 |
| Antagonist C5 | 24.7 |
| The contrast group without any additives | 12.0 |

Please refer to Table 1 which shows the experimental results of Example 1. Firstly, let's focus on the groups which are only added dispersing agent. Obviously, in the result of adding dispersing agent S100 (Di-alkyl sulfosuccinate), the deposit amount is reduced to 53%. Compared to the contrast group (100%) which is only added the culture isolated from the slime, the deposit amount is significantly different, namely, the dispersing agent (S100) has a good dispersing ability for the formation of the slime.

Moreover, in the groups which additionally add antagonist C5 after adding the dispersing agent, the deposit amount is 74.6% when the dispersing agent is B100 (Lignosulfonate), the deposit amount is 49% when the dispersing agent is S100, the deposit amount is 46% when the dispersing agent is H40 (Nonionic surfactants), the deposit amount is 105% when the dispersing agent is P100 (Polyethylene glycol), and the deposit amount is 66.4% when the dispersing agent is Bu200 (Nonionic surfactants). As shown above, these five groups show obvious reductions when compared to the contrast deposit 100%. According to the result, the addition of the antagonist C5 is positive to inhibit/reduce the slime formation. Furthermore, no matter which dispersing agent is added with the antagonist C5, after adding the antagonist C5, the deposit amount can be further reduced actually. Thus, this experiment improves that the antagonist owns the ability to reduce the slime production.

EXAMPLE 2

The Track Experiment of Periodically Adding the Antagonist

The experimental steps are described as follows:

Cultures which are isolated from the slime are cultivated in a NB cultivation liquid for 21-24 hours. Then, 1 mL culture liquids of the isolated cultures are centrifuged in 15000 rpm for 1 min and the supernatants thereof are removed. All the isolated cultures are re-suspended by adding 1 mL sterile water, and then each re-suspended culture is inoculated into a flask which already contains sterile white water 100 mL and 3 g LBKP pulp. Later, different dispersing agents are added into different flasks of each kind of culture to obtain different mixtures. The mixtures are cultivated in an incubate shaker at 40° C., 70 rpm. After being mixture cultivated for 3 hours, 3 mL antagonist C5 (*Streptomyces bikiniensis*) which has been amounted to $10^7$/mL after being cultivated for 24 hours is added thereinto to obtain another mixture. The mixture are cultivated in the incubate shaker again at 40° C., 70 rpm. After 7 days, the production of the deposit is recorded and simultaneously the antagonist C5 is re-added thereinto. Then, the final deposit amount after another 7 days (total 14 days) is also recorded.

The whole experiment is separated into four groups.

There are two contrast groups:

1: Only incubate the antagonist C5 without incubating the culture isolated from the slime; and 2: Do not incubate any culture.

There are four experimental group:

3: Only incubate the culture isolated from the slime without incubating the antagonist C5; and 4: Incubate both the culture isolated from the slime and the antagonist C5.

The groups described above are double checked and all experiments are repeated at least once. Deposit % is calculated by the formula as follows:

$$\text{Deposit}\% = \frac{\text{Deposit dry weight of experimental group}}{\text{Deposit dry weight of the culture isolated from slime}} \times 100\%$$

Results:

The experimental results of "The track experiment of periodically adding the antagonist" are shown in Table 2.

TABLE 2

The result of the track experiment of periodically adding the antagonist

| Process method | Deposit % (Day 7) | Deposit % (Day 14) |
| --- | --- | --- |
| Culture isolated from slime | 100.0 | 100.0 |
| Culture isolated from slime + Antagonist C5 | 29.0 | 87.0 |
| Culture isolated from slime + Antagonist C5 (Day 7) + Antagonist C5 | | 28.0 |
| Antagonist C5 | 31.0 | 35.0 |
| Contrast group without any additives | 27.0 | 24.0 |

Please refer to Table 2. In the group which contains the culture isolated from the slime, the deposit amount is 29% after adding the antagonist C5 and cultivating for 7 days. Compared to the contrast deposit 100% which is only added the culture isolated from slime, the difference is strictly obvious. However, the difference will be gradually reduced corresponding to the increase of the cultivation time (the deposit amount is 87% when Day 14). But, if another antagonist C5 is added at Day 7, the deposition at Day 14 (after another 7 days) will be still remained as 28% which is obviously different from the contrast deposit 100%. According to the result, the periodical addition (7 days) of the antagonist C5 is positive to inhibit/reduce the adhesion of the deposit. Consequently, if it can utilize this method of adding the antagonist C5 periodically to easily control the production of the slime, this will be a convenient and fast way for the industry. Furthermore, if take 7 days as a period, it will not be a highly concentrated time period, so that it will not consume too much labor and is really a practicable method.

In view of the aforesaid, through the proving of the experiments, the mixture of the dispersing agent and the local antagonist and the method utilizing the same according to the present invention can actually and efficiently reduce the production of the slime during the papermaking process, solve the problems caused by the slime, such as paper holes, and paper break, and further improve the quality of the paper. Moreover, the method for reducing the slime production and the mixture making the same according to the present invention can substitute for the organic biocide and will not endanger the natural environment, so that it conforms to the standard of the environmental protection and the environmental consciousness. More importantly, the present invention can easily improve the slime problem in the original papermaking process without increasing the production costs. Consequently, this is really an invention with creativity and industrial value.

While the invention has been described in terms of what are presently considered to be the most practical and preferred embodiments, it is to be understood that the invention need not be limited to the disclosed embodiment. On the contrary, it is intended to cover various modifications and similar arrangements included within the spirit and scope of the appended claims which are to be accorded with the broadest interpretation so as to encompass all such modifications and similar structures. Therefore, the above description and illustration should not be taken as limiting the scope of the present invention which is defined by the appended claims.

What we claim is:

1. A method for reducing a production of build-up slime of a papermaking material consisting essentially of a white water and a waste paper pulp in a papermaking process, comprising steps of:
   inhibiting an adhesion between a slime-producing microorganism and additives during the papermaking process by adding a dispersing agent into the papermaking material to obtain a first mixture;
   mixing and culturing the mixture;
   adding an antagonist into the first mixture to obtain a second mixture;
   mixing and culturing the second mixture for reducing the slime; and
   re-adding said antagonist into the mixed and cultured second mixture after a specific time period for further reducing the slime, wherein said antagonist is a benefit microorganism being *Streptomyces bikiniensis*.

2. The method according to claim 1, wherein the antagonist is in an amount of 107/ mL after being cultivated for 24 hrs.

3. The method according to claim 1, wherein the dispersing agent is selected from a group consisting of Lignosulfonate, Di-alkyl sulfosuccinate, and Nonionic surfactants.

4. The method according to claim 1, wherein the specific time period is seven days.

5. A method for reducing a production of build-up slime of a papermaking material consisting essentially of a white water and a leaf bleached kraft pulp in a papermaking process, comprising steps of:
   inhibiting an adhesion between a slime-producing microorganism and additives during the papermaking process by adding a dispersing agent into the papermaking material to obtain a first mixture;
   mixing and culturing the first mixture;
   adding an antagonist into the first mixture to obtain a second mixture; and
   mixing and culturing the second mixture for reducing the slime, wherein said antagonist is a benefit microorganism being *Streptomyces bikiniensis*.

6. The method according to claim 5, wherein the antagonist is in an amount of 107/ mL after being cultivated for 24 hrs.

7. The method according to claim 5, wherein the dispersing agent is selected from a group consisting of Lignosulfonate, Di-alkyl sulfosuccinate, and Nonionic surfactants.

8. A mixture for reducing a production of build-up slime in a papermaking process, comprising:
   a papermaking material consisting essentially of a white water and a leaf bleached kraft pulp;
   a dispersing agent for avoiding adhesion between a slime-causing microorganism and other additives in the mixture; and
   an antagonist being a benefit microorganism *Streptomyces bikiniensis*.

9. The mixture according to claim 8, wherein the antagonist is in an amount of 107/ mL after being cultivated for 24 hrs.

10. The mixture according to claim 8, wherein the dispersing agent is selected from a group consisting of Lignosulfonate, Di-alkyl sulfosuccinate, and Nonionic surfactants.

* * * * *